United States Patent [19]

Merger et al.

[11] Patent Number: 4,613,466

[45] Date of Patent: Sep. 23, 1986

[54] PREPARATION OF HEXAMETHYLENE 1,6-DIISOCYANATE AND/OR ISOMERIC DIISOCYANATES WHERE ALKYLENE IS OF 6 CARBON ATOMS

[75] Inventors: Franz Merger, Frankenthal; Gerhard Nestler; Friedrich Towae, both of Ludwigshafen; Hans Hellbach, Lampertheim, all of Fed. Rep. of Germany

[73] Assignee: BASF Aktiengesellschaft, Ludwigshafen, Fed. Rep. of Germany

[21] Appl. No.: 754,751

[22] Filed: Jul. 15, 1985

Related U.S. Application Data

[63] Continuation-in-part of Ser. No. 515,896, Jul. 21, 1983, abandoned.

[30] Foreign Application Priority Data

Jul. 24, 1982 [DE] Fed. Rep. of Germany ....... 3227748
Dec. 24, 1982 [DE] Fed. Rep. of Germany ....... 3248018

[51] Int. Cl.$^4$ ........................................... C07C 141/00
[52] U.S. Cl. .................................................. 560/344
[58] Field of Search ..................................... 260/453 P

[56] References Cited

U.S. PATENT DOCUMENTS

| | | | |
|---|---|---|---|
| 3,734,941 | 5/1973 | Sydor | 260/453 P |
| 4,322,365 | 3/1982 | Merger et al. | 260/453 P |
| 4,388,246 | 6/1983 | Sundermann | 260/453 P |

*Primary Examiner*—Alan Siegel
*Attorney, Agent, or Firm*—Keil & Weinkauf

[57] ABSTRACT

Hexamethylene 1,6-diisocyanate and/or isomeric aliphatic diisocyanates where alkylene is of 6 carbon atoms, preferably 2-methylpentamethylene 1,5-diisocyanate and/or 2-ethyltetramethylene 1,4-diisocyanate, are prepared by a process wherein the corresponding dialkylurethanes are vaporized, without decomposition, at from 220° to 300° C., advantageously under reduced pressure, the dialkylurethane vapors are subjected to thermal cleavage under reduced pressure, preferably from 0.1 to 200 mbar, and at above 300° C., preferably from 310° to 480° C. The cleavage products are fractionally condensed with the product obtained in the first condensation stage consisting predominantly of the diisocyanates, while that obtained in the second condensation stage is the alcohol.

9 Claims, No Drawings

PREPARATION OF HEXAMETHYLENE 1,6-DIISOCYANATE AND/OR ISOMERIC DIISOCYANATES WHERE ALKYLENE IS OF 6 CARBON ATOMS

This application is a continuation-in-part of application Ser. No. 515,896, filed July 21, 1983, now abandoned.

Industrial production of hexamethylene 1,6-diisocyanate is based on phosgenation of hexamethylenediamine to give hexamethylene dicarbamic acid chloride and thermal cleavage of the latter to give hexamethylene 1,6-diisocyanate and hydrogen chloride. Apart from the serious problems in respect of environmental protection and safety which are associated with the use of phosgene, this method has still further critical disadvantages. For example, the space-time yields in the production of hexamethylene 1,6-diisocyanate are very moderate. In addition to hexamethylene 1,6-diisocyanate, the process gives a number of by-products, of which the most important, 6-chlorohexyl isocyanate, furthermore has the disadvantage that it requires a very expensive distillation procedure to separate it off from the hexamethylene 1,6-diisocyanate.

It is known that N-substituted aromatic urethanes can be thermally cleaved in the gas phase or in the liquid phase to give isocyanates. However, thermal cleavage is accompanied by various undesirable side-reactions in many cases, for example the decarboxylation reaction of the urethanes, which may be accompanied by the formation of primary and secondary amines and of olefins, and the reaction of the resulting isocyanate with the urethane to give an allophanate, or with an amine to give a urea, and the polymerization of the isocyanates to isocyanurates.

According to German Published Application No. DAS 1,944,719 (British Pat. No. 1,247,451), the pyrolysis of urethanes in the vapor phase is carried out at from 400° to 600° C. in the presence of a Lewis acid as a catalyst, and the isocyanate and alcohol are separated by fractional condensation. Toluylene 2,4-diisocyanate is obtained, for example, by pyrolysis of toluylene-2,4-diethylurethane in the presence of iron(III) chloride. Disadvantages of the reaction include the low yields, which are associated with substantial amounts of a polymeric by-product, decomposition of the catalyst and corrosion of the reaction apparatus. German Laid-Open Application DOS No. 2,410,505 (U.S. Pat. No. 3,870,739) describes a process in which an aromatic urethane is cleaved at from 350° to 550° C. and under a pressure of less than (m+1) times the isocyanate vapor pressure in a catalyst-free pyrolysis zone in the course of 15 seconds. One of the disadvantages of this process is that it is difficult to carry out by a continuous procedure because a solid polymer is obtained as a by-product and has to be separated off.

According to German Laid-Open Application DOS No. 2,635,490 (U.S. Pat. No. 4,081,472), aromatic isocyanates are prepared by a method in which urethanes are brought into contact, at 150°-350° C. and under reduced pressure, with a solution of, as the catalyst, one or more metal ions, e.g. ions of copper, zinc, aluminum, tin, titanium, vanadium, iron, cobalt and nickel, in a solvent with a boiling point of 200° C., the metal concentration being not less than 0.001% by weight, based on the solvent. The resulting cleavage products are separated by fractional condensation. In this procedure, however, small amounts of non-distillable polymers are formed, and these remain in the catalyst-containing solvent residue; this makes it necessary to use a purifying agent after some time.

According to German Laid-Open Application DOS No. 2,942,543 (U.S. Pat. No. 4,330,479), very good results are obtained in the cleavage reaction if aromatic urethanes are cleaved over catalytically active metals which have a large surface area and are present in the heterogeneous phase. The disadvantage of this process is that the metals used as catalysts become coated and therefore lose their catalytic activity over a period of time, with the result that, in this case too, additional purifying operations are required.

According to German Laid-Open Application DOS No. 3,142,627, this deficiency can be overcome by carrying out the thermal cleavage in the presence of carbon, preferably in the form of a fat in a fluidized bed. The advantage of this process is that it is not necessary to regenerate the catalyst after it has been deactivated by polymeric by-products or decomposition products; instead, it can be destroyed by incineration by a procedure which causes no pollution and leaves no residue. However, the yields of hexamethylene diisocyanate are below 90% in all cases.

From the above statements, it is clear that some of the conventional processes for the preparation of isocyanates possess substantial deficiencies. The Examples of the above publications describe almost exclusively the cleavage of aromatic urethanes and therefore suggest that a satisfactory industrial production of aliphatic diisocyanates cannot be achieved in this manner.

It is an object of the present invention to provide an improved, economical process, which causes little pollution, for the preparation of hexamethylene 1,6-diisocyanate and/or isomeric aliphatic diisocyanates where alkylene is of 6 carbon atoms (hereinafter referred to as diisocyanates for short).

We have found that this object is achieved, and that, surprisingly, under certain reaction conditions hexamethylenedialkylurethanes and/or the corresponding aliphatic isomers can be thermally cleaved by a simple industrial procedure to give diisocyanates in very good yields.

The present invention accordingly relates to a process for the preparation of hexamethylene 1,6-diisocyanate and/or isomeric aliphatic diisocyanates where alkylene is of 6 carbon atoms by thermal cleavage of the corresponding dialkylurethanes, wherein the latter are vaporized, without decomposition, at from 220° to 300° C. in a vaporizer and are thermally cleaved in the gas phase at above 300° C. under reduced pressure, and the gases produced in the cleavage reaction are fractionally condensed.

Isomeric aliphatic diisocyanates where alkylene is of 6 carbon atoms are, in particular, 2-methylpentamethylene 1,5-diisocyanate and 2-ethyltetramethylene 1,4-diisocyanate. Accordingly, the novel process is preferably used for the preparation of the two above-mentioned isomers and in particular of hexamethylene 1,6-diisocyanate, as well as mixtures of these.

In principle, all hexamethylenedialkylurethanes and/or isomeric aliphatic dialkylurethanes where alkylene is of 6 carbon atoms and alkyl is of 1 to 8 carbon atoms, or mixtures of these, are suitable starting materials for the novel process. Isomeric aliphatic dialkylurethanes where alkylene is of 6 carbon atoms are referred to hereinafter as diurethanes for short. Preferably used starting materials are those which satisfy the following requirements:

(a) the diurethane must be capable of vaporization without decomposition,
(b) the boiling points of the cleavage products, i.e. the diisocyanate and the alcohol, must be sufficiently far apart to obtain a highly quantitative separation of the two end products via fractional condensation, and
(c) to avoid loss of material, the alcohol eliminated must be capable of condensation in a highly quantitative manner in a second condensation stage, using methods which can be realized industrially.

The stated requirements are satisfied, for example, by diurethanes where alkyl is of 1 to 5 carbon atoms, e.g. hexamethylenedimethylurethane, hexamethylenediethylurethane, hexamethylenedipropylurethane, hexamethylenedi-n-butylurethane, hexamethylenediisobutylurethane, hexamethylenedi-n-pentylurethane and hexamethylenediisopentylurethane, as well as the corresponding 2-methylpentamethylene-1,5-dialkylurethane and/or 2-ethyltetramethylene-1,4-dialkylurethane isomers, so that these diurethanes are preferably used. Very particularly advantageous results were obtained in the thermal cleavage of hexamethylene-1,6-, 2-methylpentamethylene-1,5- and 2-ethyltetramethylene-1,4-di-n-butylurethane and/or -diisobutylurethane, so that these dialkylurethanes are employed in particular. The diurethanes can be prepared by a conventional process. They are obtained in very good yields and free of phosgene by, for example, reacting aliphatic diamines where alkylene is of 6 carbon atoms with urea or urea/O-butylcarbamate mixtures in the presence of butanol, as described in German Laid-Open Application DOS Nos. 2,917,490 or DOS 2,917,493.

Although not essential, in some instances it may be advantageous to carry out the thermal cleavage in the presence of a hydrogen halide and/or a donor which forms hydrogen halide under the reaction conditions. When using this option, the hydrogen halide is employed in an amount of from 0.001 to 1.0, preferably from 0.002 to 0.2 mole percent per mole of diurethane. If on the other hand a hydrogen halide donor is used, this is employed in an amount such that from 0.001 to 1.0, preferably from 0.002 to 0.2, mole percent of hydrogen halide is formed under the conditions of the cleavage reaction. The hydrogen halide or donor can be mixed with the diurethanes prior to or after introduction into the vaporizer, or alternatively metered directly into the cleavage reactor during thermal cleavage.

The diurethanes can be introduced into the vaporizer in liquid or solid form, for example as a melt or powder, or even as a suspension or solution in a solvent which is inert under the reaction conditions.

The vaporizer is operated at from 220° to 300° C., preferably from 240° to 280° C., and under a pressure of from 0.1 to 200, preferably from 5 to 100, mbar, and a thin-film vaporizer has proved particularly useful.

If an adequate amount of heat is supplied, the total amount of diurethane introduced can be vaporized. However, we have found that it is advantageous if some of the diurethane is not vaporized but is discharged from the reactor as a melt, since this has the effect of cleaning the vaporizer wall. The weight ratio of vaporized to non-vaporized diurethane is as a rule from 20:80 to 90:10, preferably from 40:60 to 60:40.

The diurethane vapors are then fed into the cleavage reactor, where cleavage is carried out at above 300° C., preferably from 310° to 480° C., in particular from 360° to 440° C., either batchwise or continuously, under reduced pressure, preferably from 0.1 to 200, in particular from 1 to 100, mbar.

The cleavage reactor is generally in the form of a column and may have any desired cross-section. Preferably, a long, cylindrical cleavage reactor is used. The ratio of the internal diameter to the length of the cleavage reactor is in general from 1:2 to 1:1,000, preferably from 1:10 to 1:500. The cleavage reactor may be vertical or horizontal, or may assume an intermediate position. A preferably used cleavage reactor is a tube furnace in which the internal diameter of the tube is about 10-100 mm and the length of the tube about 0.5-5 m.

It has been found that especially good results are obtained when the cleavage is carried out in the presence of a thermally stable reactor packing consisting of brass, zinc or zinc alloyed with nickel and copper. In the latter alloy, the proportion of components per 100 parts by weight is 45-67 parts by weight of copper, 12-45 parts by weight of zinc, and 10-26 parts by weight of nickel. These materials must permit the passage of gases and are desirably in the form of beads, rings and/or chips.

The dissociation products present in the vapor phase, which consist almost exclusively of diisocyanate and alcohol, are fed from the cleavage reactor to a two-stage vapor condensation apparatus. In the first condensation stage, which, depending on the system pressure of from 0.1 to 100 mbar, is operated at from 60° to 120° C., the diisocyanate condenses virtually completely. In the case of hexamethylene-1,6-dibutylurethane, which is preferably used, and under a system pressure of, for example, from 20 to 40 mbar, the condensation temperature is advantageously maintained at from 70° to 100° C. The temperature in the second condensation stage depends on the boiling point of the alcohol formed. In the cleavage of hexamethylene-1,6-dibutylurethane, for example, the condensation temperature is advantageously brought to 5°-30° under the above system pressure.

The alcohol obtained in the second condensation stage can, for example, be re-used for the preparation of the diurethane, without being purified beforehand.

The diisocyanate obtained in the first condensation stage is usually purified by distillation, after which it has a purity of about 99.5% by weight.

Diisocyanates obtained by the novel process are very useful for the production of polyurethane or polyurethane/polyurea plastics and in particular for light-stable polyurethane finishes and coatings.

In the Examples which follow, parts are by weight.

EXAMPLE 1

The entire cleavage apparatus, comprising a thin-film vaporizer, a cleavage reactor and a two-stage vapor condensation apparatus, was evacuated down to 20-22 mbar.

1,200 parts of hexamethylenedi-n-butylurethane in the form of a melt were introduced into a thin-film vaporizer heated at 260° C., in the course of 4.5 hours, so that 591 parts flowed away and 609 parts were vaporized. The hexamethylenedi-n-butylurethane vapors passed into a cleavage reactor which had an empty space of about 1 liter and was packed with brass rings of 3 mm diameter. The average temperature in the cleavage reactor was 370° C. The gases produced in the cleavage reaction and emerging from the reactor were fractionally condensed in the downstream two-stage condensation apparatus. In the first condenser, which was operated at 85° C., 273 parts of hexamethylene diisocyanate (HDI) and 17 parts of butoxycarbonylaminohexamethylene isocyanate were obtained. In the second condenser, which was operated at 10°–12° C., 240 parts of n-butanol and 68 parts of hexamethylenedibutylurethane were obtained, the latter product being formed as a result of recombination of entrained HDI with butanol.

The selectivity of the cleavage was therefore 94.9% with respect to HDI, 4.1% with respect to recyclable butoxycarbonylaminohexamethylene isocyanate and 96.8% with respect to butanol.

EXAMPLE 2

The entire cleavage apparatus, comprising a thin-film vaporizer, a cleavage reactor and a two-stage vapor condensation apparatus, was evacuated down to 20–22 mbar.

5,600 parts of hexamethylenedi-n-butylurethane in the form of a melt were introduced into a thin-film vaporizer heated at 260° C., in the course of 21 hours, so that 2,738 parts flowed away and 2,862 parts were vaporized. The hexamethylenedi-n-butylurethane vapors passed into a cleavage reactor which had an empty space of about 1 liter and was packed with brass rings of 3 mm diameter. The average temperature in the cleavage reactor was 370° C. under a pressure of 20–30 mbar. In addition, 0.263 part of hydrogen chloride mixed with 5 parts by volume of nitrogen was fed into the reactor via a fine metering valve. The products emerging from the first condenser, which was operated at 85° C., were removed every 3 hours and tested in respect of their isocyanate content. Table 1 shows the ratio (in parts) of hexamethylene 1,6-diisocyanate (HDI-1,6) to butoxycarbonylaminohexamethylene isocyanate (monoisocyanate) as a function of the reaction time. No significant variation in the ratio is detectable.

TABLE 1

| Time [h] | 3 | 6 | 9 | 12 | 15 | 18 | 21 |
|---|---|---|---|---|---|---|---|
| HDI-1,6 [parts] | 91.3 | 92.7 | 91.6 | 89.3 | 92.8 | 88.1 | 90.6 |
| Monoisocyanate [parts] | 8.7 | 7.3 | 8.4 | 10.7 | 7.2 | 11.9 | 9.4 |

EXAMPLE 3

The cleavage apparatus described in Example 1 was evacuated down to 9–11 mbar.

1500 parts of hexamethylenedi-n-butylurethane in the form of a melt were introduced into a thin-film vaporizer heated at 246°–248° C., in the course of 5.5 hours, so that 738 parts flowed away and 762 parts were vaporized. The hexamethylenedi-n-butylurethane vapors passed into a cleavage reactor which had an empty space of about 1 liter and was packed with zinc-coated stainless steel rings of 3 mm diameter. The average temperature in the cleavage reactor was 380° C. The gases produced in the cleavage reaction and emerging from the reactor were fractionally condensed in the downstream two-stage condensation apparatus. In the first condenser, which was operated at 75° C., 335 parts of hexamethylene diisocyanate (HDI) and 26 parts of butoxycarbonylaminohexamethylene isocyanate were obtained. In the second condenser, which was operated at 0°–3° C., 290 parts of n-butanol and 90 parts of hexamethylenedibutylurethane were obtained, the latter product being formed as a result of recombination of entrained HDI with butanol.

The selectivity of the cleavage was therefore 93.8% with respect to HDI, 5.0% with respect to recyclable butoxycarbonylaminohexamethylene isocyanate and 95.7% with respect to butanol.

What is claimed is:

1. A process for the preparation of hexamethylene 1,6-diisocyanate and isomeric aliphatic diisocyanates where the alkylene is of 6 carbons by thermal cleavage of the corresponding dialkylurethanes, which comprises:
    (a) vaporizing said dialkylurethanes, without decomposition, at from 220° to 300° C. in a vaporizer,
    (b) passing the resulting vapors into a reactor provided with a packing material selected from the group consisting of brass, zinc, and zinc alloyed with nickel and copper,
    (c) thermally cleaving said vaporous dialkylurethanes in the packed reactor at a temperature above 300° C. under a reduced pressure, and
    (d) causing the vapors produced in the cleavage reaction to be fractionally condensed.

2. A process in accordance with claim 1, wherein the cleavage is carried out at from 310° to 480° C.

3. A process according to claim 1, wherein the cleavage is carried out under a pressure of from 0.1 to 200 mbar.

4. A process in accordance with claim 1, wherein the cleavage products are separated by fractional condensation in a series of condensers.

5. A process in accordance with claim 1, wherein the dialkylurethane employed in the procedure is selected from the group consisting of hexamethylene-1,6-, 2-methylpentamethylene-1,5-, 2-ethyltetramethylene-1,4-dimethylurethane, -diethylurethane, -dipropylurethane, -di-n-butylurethane, -diisobutylurethane, -di-n-pentylurethane and -diisopentylurethane.

6. A process in accordance with claim 1, wherein the isomeric aliphatic diisocyanate product obtained is 2-methylpentamethylene 1,5-diisocyanate and/or 2-ethyltetramethylene 1,4-diisocyanate.

7. A process in accordance with claim 1, wherein the reactor is packed with zinc-coated stainless steel rings.

8. A process in accordance with claim 1, wherein the reactor is packed with an alloy of zinc, nickel and copper with the proportions of components per 100 parts by weight being 12–45 parts by weight of zinc, 10–26 parts by weight of nickel and 45–67 parts by weight of copper.

9. A process in accordance with claim 1, wherein the reactor is packed with brass rings.

* * * * *